(12) United States Patent
Zhang (10) Patent No.: US 8,255,038 B2
(45) Date of Patent: Aug. 28, 2012

(54) SYSTEM AND METHOD FOR NON-UNIFORM IMAGE SCANNING AND ACQUISITION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 380 days.

(21) Appl. No.: 12/547,327

(22) Filed: Aug. 25, 2009

(65) Prior Publication Data

US 2010/0056897 A1 Mar. 4, 2010

Related U.S. Application Data

(60) Provisional application No. 61/092,474, filed on Aug. 28, 2008.

(51) Int. Cl.
*A61B 6/00* (2006.01)

(52) U.S. Cl. ........................................ 600/428; 600/413

(58) Field of Classification Search .................. 600/413, 600/428, 481, 500, 504, 508, 509, 521
See application file for complete search history.

(56) References Cited

U.S. PATENT DOCUMENTS

| | | | |
|---|---|---|---|
| 5,229,668 A | 7/1993 | Hughes et al. | |
| 5,565,914 A | 10/1996 | Motta | |
| 5,778,294 A | 7/1998 | Hiraoka et al. | |
| 5,832,051 A | 11/1998 | Lutz | |
| 5,854,656 A | 12/1998 | Noggle | |
| 5,872,572 A | 2/1999 | Rossignac | |
| 6,154,516 A | 11/2000 | Heuscher et al. | |
| 6,275,560 B1 | 8/2001 | Blake et al. | |
| 6,393,091 B1 | 5/2002 | Slack et al. | |
| 6,411,740 B1 | 6/2002 | Daly et al. | |
| 6,477,553 B1 | 11/2002 | Druck | |
| 6,614,448 B1 | 9/2003 | Garlick et al. | |
| 6,708,052 B1 | 3/2004 | Mao et al. | |
| 6,895,077 B2 | 5/2005 | Karellas et al. | |
| 7,031,504 B1 | 4/2006 | Argiro et al. | |

*Primary Examiner* — Ruth S Smith
(74) *Attorney, Agent, or Firm* — Alexander J Burke (57) ABSTRACT

A system employs non-uniform and nonlinear patient monitoring signals in automatically adaptively varying image resolution, image scanning frequency and acquisition speed and gates and synchronizes the image scanning and acquisition of an imaging system. A system acquires medical images of patient anatomy using a trigger generator. The trigger generator generates a trigger signal comprising a non-periodic sequence of pulses in a first signal portion within individual heart beat cycles. The first signal portion is periodically repeated for multiple sequential individual heart beat cycles. An image acquisition device acquires multiple images of a patient anatomical portion in response to corresponding multiple individual pulses of the non-periodic sequence of pulses. A display processor presents acquired images on a display for review by a user.

17 Claims, 5 Drawing Sheets

SYSTEM AND METHOD FOR NON-UNIFORM IMAGE SCANNING AND ACQUISITION

This is a non-provisional application of provisional application Ser. No. 61/092,474 filed Aug. 28, 2008, by H. Zhang.

FIELD OF INVENTION

This invention concerns a system for acquiring a non-periodic sequence of medical images of patient anatomy for display for review by a user.

BACKGROUND OF INVENTION

Continuous image scanning and data acquisition is used in current clinical applications, especially cardiac examination and treatment. Known image quality and acquisition improvement systems attempt to avoid problems involved in cardiac tissue movement, such as during depolarization and repolarization phases of a heart cycle. Some known systems involve use of surface ECG signals (R wave) and respiration signals to gate image acquisition to avoid patient movement noise and artifacts. Imaging of cardiac function is of value at the time of cardiac tissue contraction and during other functional phases. Known systems employ patient functional signals in image scanning and acquisition, such as imaging for Atrium contraction, imaging for ventricle maximum volume measurement and left ventricular artery function (e.g. LAD ischemia detection). Patient functional signals include body surface ECG signals, intra-cardiac electrograms (ICEG), hemodynamic signals (such as invasive and non-invasive blood pressures), and vital signals (such as respiration, blood oxygen saturation (SPO2)), for example. Cardiac function signals can identify an accurate time and heart cycle phase for image acquisition gating and synchronizing for capturing and characterizing cardiac functions and tissue activities. The use of cardiac function signals in imaging supports objective and accurate diagnosis and medical treatment.

Known image scanning and acquisition systems can continuously monitor a patient organ and tissue involving movement such as of blood flow in coronary arteries during injection of a contrast agent (dye) in a heart, for example. However, in known systems, an image scanning trigger is typically fixed and image acquisition consequently misses some important stages and times of cardiac function analysis due to the time between image acquisitions. Known systems fail to provide a comprehensive method of triggering image scanning and acquisition based on cardiac function signals, such as EP signals for chamber and tissue activity evaluation, Hemodynamic pressure signals for determination of maximum volume of ventricle and blood flow and respiration signals for artifact avoidance. Further, in known systems, during image continuous acquisition, the image resolution, scanning speed (rate) and sensitivity is not controllable after initiation of an image scanning procedure. Known continuous image scanning methods use imaging hardware inefficiently and acquire redundant images during a rest phase of the heart (without contraction activity), for example. Also known continuous image scanning methods increase patient radiation exposure. A system according to invention principles addresses these requirements and associated deficiencies and problems.

SUMMARY OF INVENTION

A system employs non-uniform and nonlinear patient monitoring signals (e.g., ECG signal amplitude/frequency, hemodynamic pressure, vital signs) in automatically adaptively varying image resolution, image scanning frequency and acquisition speed of an imaging system such as an X-ray system, in response to cardiac functions. A system acquires medical images of patient anatomy using a trigger generator. The trigger generator generates a trigger signal comprising a non-periodic sequence of pulses in a first signal portion within individual heart beat cycles. The first signal portion is periodically repeated for multiple sequential individual heart beat cycles. An image acquisition device acquires multiple images of a patient anatomical portion in response to corresponding multiple individual pulses of the non-periodic sequence of pulses. A display processor presents acquired images on a display for review by a user.

DETAILED DESCRIPTION OF THE INVENTION

A system uses cardiac functional signals (e.g., ECG signal amplitude or frequency, hemodynamic pressure, vital sign signals including respiration signals) in non-uniform and nonlinear image acquisition and scanning. The image resolution, scanning frequency and acquisition speed of an imaging system, such as an X-ray image system, is automatically adaptively, programmed in response to cardiac functions. For example, during a rest stage of a heart (which is greater than 50% of a whole heart cycle), high resolution and less frequent image acquisition is used to improve image quality and system usage efficiency and reduces redundant image scanning and power usage. Further, the system improves patient safety by employing reduced radioactivity dosage. The system adaptively adjusts imaging parameters during continuous image acquisition, such as for noisy and fast image acquisition for abnormal tissue problem tracking, in response to the type of clinical application involved. In heart monitoring, image scanning and acquisition is synchronized with cardiac movement. In order to compare volume changes of a specific heart chamber at different stages (before and after a clinical procedure, such as medicine injection), the system acquires images triggered by a cardiac function signal. Specifically, for right atrial activity imaging, the system acquires images triggered by a P wave and for left ventricle imaging for maximum size and volume diagnosis, the system acquires images triggered by EoD (end-diastolic) pressure.

Figure 1:
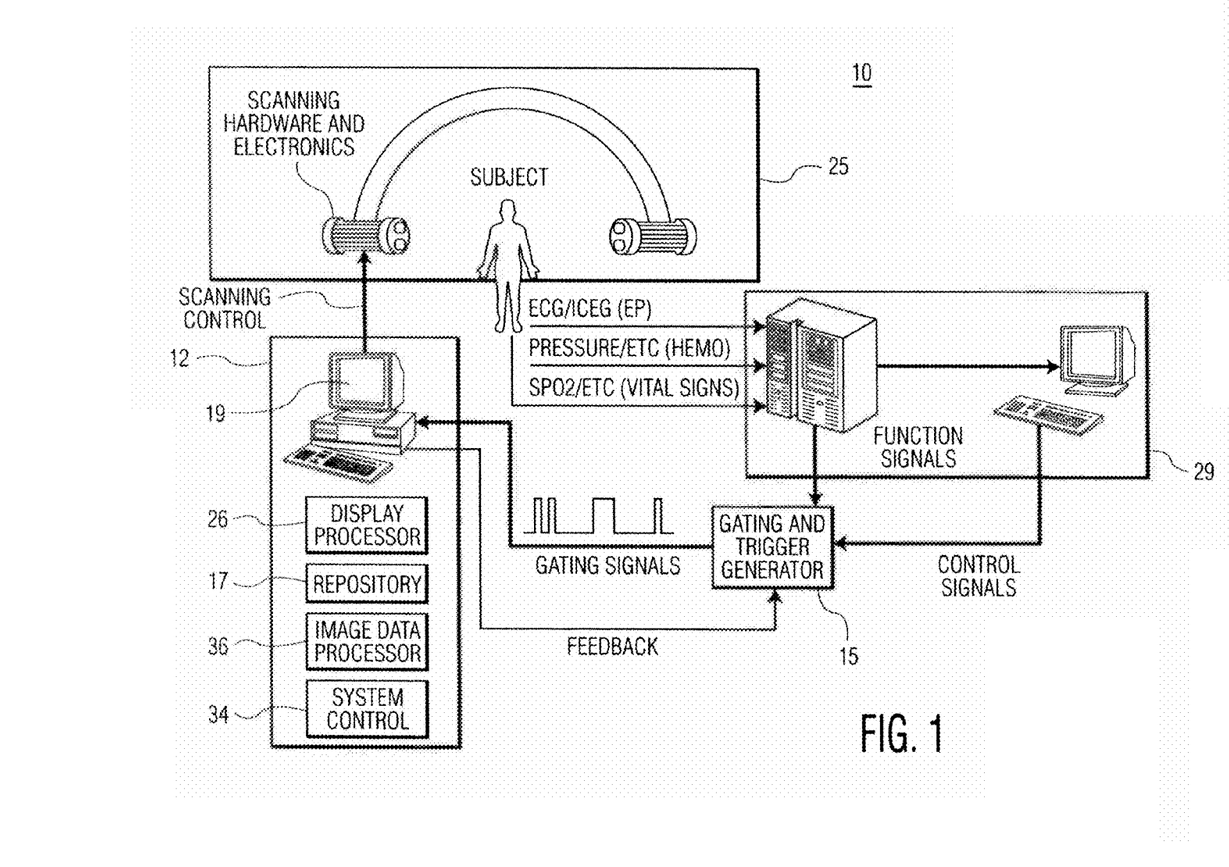
FIG. 1 shows an image acquisition system, according to invention principles.

FIG. 1 shows image acquisition system 10 for acquiring medical images of patient anatomy. System 10 includes one or more processing devices (e.g., workstations, computers or portable devices such as notebooks, Personal Digital Assistants) 12 that individually include at least one repository 17, image data processor 36, system and imaging control unit 34 and display processor 26 enabling user interaction with a Graphical User Interface (GUI). Display 19 supports GUI and medical image presentation in response to predetermined user (e.g., physician) specific preferences. System 10 also includes, trigger generator 15, patient monitoring system 29 and imaging device 25. System and imaging control unit 34 controls operation of imaging device 25 for performing image acquisition of patient anatomy in response to user command. Imaging device 25 may comprise an X-ray imaging device (e.g., a mono-plane or biplane X-ray imaging system), a CT scanning device, MR imaging device or Ultrasound imaging system, for example. The units of system 10 intercommunicate via a network (not shown to preserve drawing clarity). At least one repository 17 stores medical image studies for patients in DICOM compatible (or other) data format. A medical image study individually includes multiple image series of a patient anatomical portion which in turn individually include multiple images.

Trigger generator 15 generates a trigger signal comprising a non-periodic sequence of pulses in a first signal portion within individual heart beat cycles. The first signal portion is periodically repeated for a plurality of sequential individual heart beat cycles. Image acquisition device 25 acquires multiple images of a patient anatomical portion in response to corresponding multiple individual pulses of the non-periodic sequence of pulses. Trigger generator 15 derives a trigger signal from signals acquired by patient signal monitoring system 29 and the derived trigger signal is used to control and adapt image scanning and acquisition. Generator 15 provides uniform and non-uniform trigger signals in response to data indicating a type of clinical application. A feedback signal is provided by processing device 12 to generator 15 to compensate for circuit and processing delay to ensure accuracy of timing of image acquisition. Display processor 26 presents acquired images on display 19 for review by a user. System 10 provides cardiac function signal based non-uniform (controllable and adaptive to clinical function) image acquisition, which facilitates capturing desired heart stage and functional movement events. System 10 adaptively varies image scanning parameters, including image resolution, scanning speed and rate and sensitivity, in response to a desired clinical application by selection and use of one or more particular cardiac function signals used by unit 15 to derive a trigger pulse sequence, from multiple available different signals. System 10 adaptively switches between high resolution image acquisition with relatively slow scanning speed for a static rest phase portion of a heart cycle and a low resolution image acquisition with relatively fast scanning speed for an active heart cycle phase, in response to derived trigger signals.

Image data processor 36 provides image data processing including mapping of image points to a location and time corresponding to a 3D imaging volume representation of a heart position and registration (alignment) of different images to support heart condition diagnosis. System 10 non-uniform image scanning also supports tissue function diagnosis, such as to identify cardiac chamber maximum volume in response to blood pressure signals with respiratory motion artifact and noise reduced using a respiratory signal responsive image acquisition trigger. Trigger generator 15 adaptively derives a trigger signal in response to data indicating a type of clinical application and procedure, such as by using an intra-cardiac blood pressure (hemodynamic) based trigger for heart chamber volume estimation and by using an intra-cardiac electrogram (electrophysiological) and vital signal based trigger for motion tolerant image acquisition, for example. Trigger generator 15 adaptively derives a trigger based on at least one of, hemodynamic signals (invasive blood pressure, non-invasive blood pressure, blood flow rate), electrophysiological signals (surface ECG, EP frequency signals, derived power and spectrum signals, intra-cardiac electrograms, unipolar and bipolar signals), and vital sign signals (blood oxygen saturation SPO2, respiration blood pressure acceleration) signals.

Figure 2:
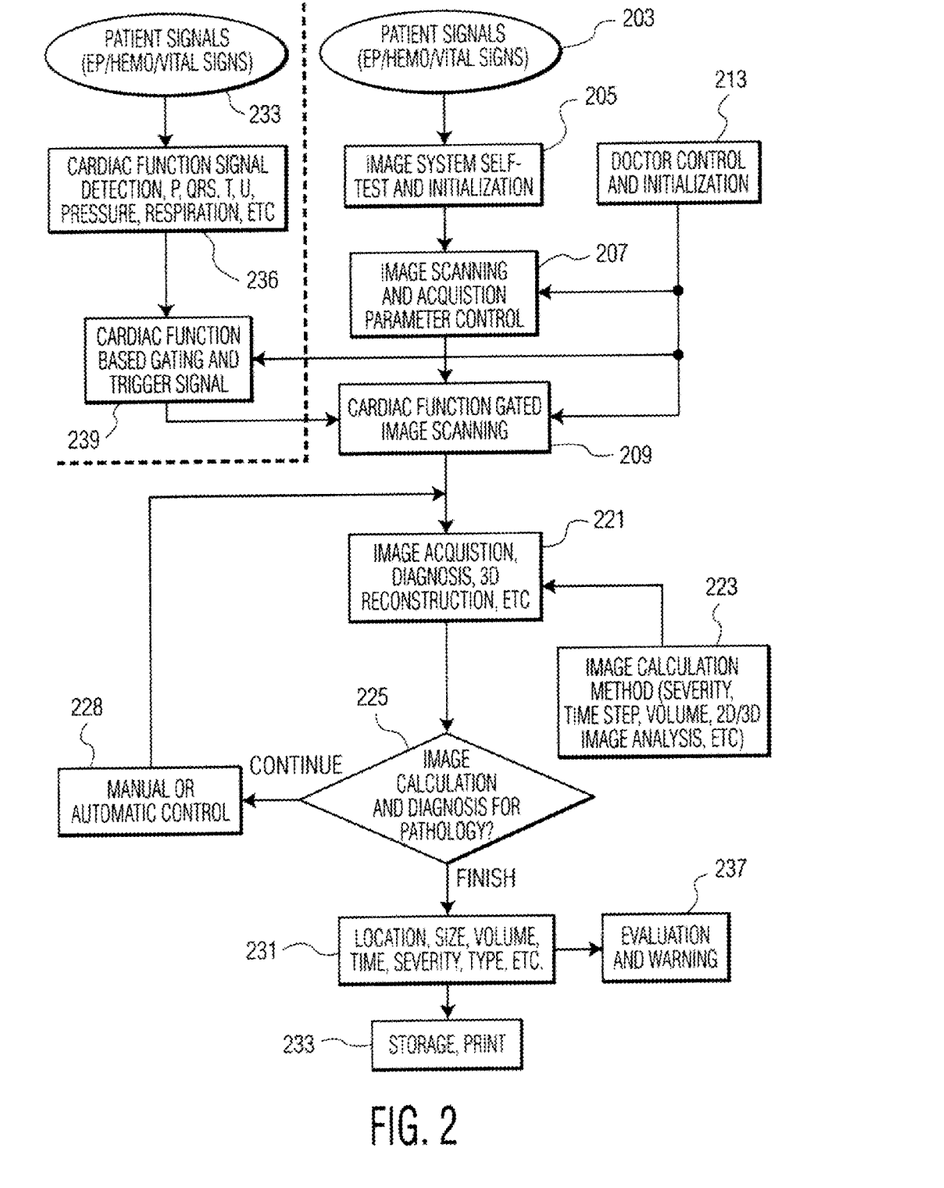
FIG. 2 shows a process and workflow of cardiac function signal based image gating and acquisition employed by an image acquisition system, according to invention principles.

FIG. 2 shows a process and workflow of cardiac function signal based image gating and acquisition employed by image acquisition system 10 (FIG. 1). System 10 image scanning and acquisition parameters are adaptively selected and adjusted. Patient monitoring system 29 acquires, buffers and digitizes patient monitoring signals in step 203 and applies the signals for initializing and testing imaging device 25 in step 205. Image scanning and acquisition parameters including image resolution and scanning rate that vary over the duration of one or more heart cycles are adaptively determined and set in step 207. These parameters are set in response to predetermined selected configuration data of a physician or configuration data associated with a particular clinical procedure, diagnosis or imaging characteristics, and data indicating a type of clinical procedure and/or user entered data and commands provided in step 213. Similarly, in step 233, Patient monitoring system 29 acquires, buffers and digitizes patient monitoring signals in step 233 for processing in step 236 to derive cardiac function signals including P, QRS, T, U wave portions of an ECG signal as well as to derive signals indicative of portions of blood pressure and respiratory signals, for example. Trigger generator 15 (FIG. 1) in step 239 (FIG. 2) adaptively derives a trigger signal in response to predetermined selected configuration data of a physician or configuration data associated with a particular clinical procedure, or data indicating a type of clinical application and procedure acquired in step 213. Trigger generator 15 adaptively derives a trigger comprising a non-periodic sequence of pulses using least one of, the derived derive cardiac function signals, hemodynamic signals (invasive blood pressure, non-invasive blood pressure, blood flow rate), electrophysiological signals (surface ECG, EP frequency signals, power and spectrum calculation signals, intra-cardiac electrograms, unipolar and bipolar signals), and vital signs signals (blood oxygen saturation SPO2, respiration blood pressure acceleration) signals. The cardiac function gating and synchronization signals may comprise derived signals that are derived from a cardiac function such as blood pressure acceleration signals and EP frequency signals, signal energy, spectrum, dominant time/frequency components or signals directly acquired from a patient (waveform or sync pulse).

Image acquisition device 25 in step 209 performs X-ray (or other) image acquisition gated and synchronized using trigger signals comprising non-periodic sequence of pulses derived in step 239 and in response to predetermined selected configuration data of a physician or configuration data associated with a particular clinical procedure, or data indicating a type of clinical application and procedure acquired in step 213. System 10 tunes image scanning and acquisition (of uni-plane or bi-plane X-ray system 25) based on the signals and data acquired in step 213, to obtain an optimum image for a specific application such as for maximum chamber volume calculation with motion noise rejection. Image acquisition device 25 adapts image resolution, image sensitivity, radiation exposure time and imaging device operational speed, of at least one image of multiple images in response to multiple individual pulses of the non-periodic sequence of pulses. Two dimensional (2D) X-ray images acquired by acquisition device 25 are processed in step 221 to reconstruct a 3D imaging volume dataset and facilitate qualitative and quantitative diagnosis and characterization of abnormal cardiac functions and pathologies. In step 223 image data processor 36 selects a process to use for analysis of an acquired image to determine, medical condition, severity, time step used between image acquisition, chamber volume and to derive a 3D image reconstruction from a 2D image, for example. Selectable processes include a process for chamber edge determination for maximum chamber area and volume analysis and image registration for vessel and chamber analysis.

In step 225 image data processor 36 uses a selected process to analyze an acquired image to determine image associated parameters and calculate image associated values and identify a particular medical condition by mapping determined parameters and calculated values to corresponding value ranges associated with medical conditions using mapping information in repository 17. Processor 36 also determines medical condition severity, chamber volume and derives a 3D image reconstruction from a 2D image, for example. Steps 221 and 225 are iteratively repeated in response to manual or automatic direction in step 228 to identify medical condition characteristics in one or more different acquired images. In response to completion of iterative image analysis of steps 221, 225 and 228, processor 36 in step 231 determines location, size, volume, severity and type of medical condition as well as a time within a heart cycle associated with a medical condition. Processor 36 initiates generation of an alert message for communication to a user in step 237 and provides medical information for use by a physician in making treatment decisions. Display processor 26 in step 233 presents images, acquired by acquisition device 25 to a user on a reproduction device such as display 19 or a printer and stores images in repository 17.

In response to a determined type of clinical application, system 10 adaptively selects synchronization signal (trigger signal) timing from multiple synchronization arrangements using cardiac function signals based image acquisition. The trigger signal enables adaptive variation in timing of image acquisition within successive heart cycles of each individual image frame of multiple sequential image frames. In order to characterize cardiac function (such as for chamber and tissue evaluation of cardiac patients who have hypertension), system 10 enables acquisition of a single image to diagnose hypertension effects. Thereby system 10 reduces complexity of a corresponding medical procedure and associated risk of overdose of radiation.

Figure 3:
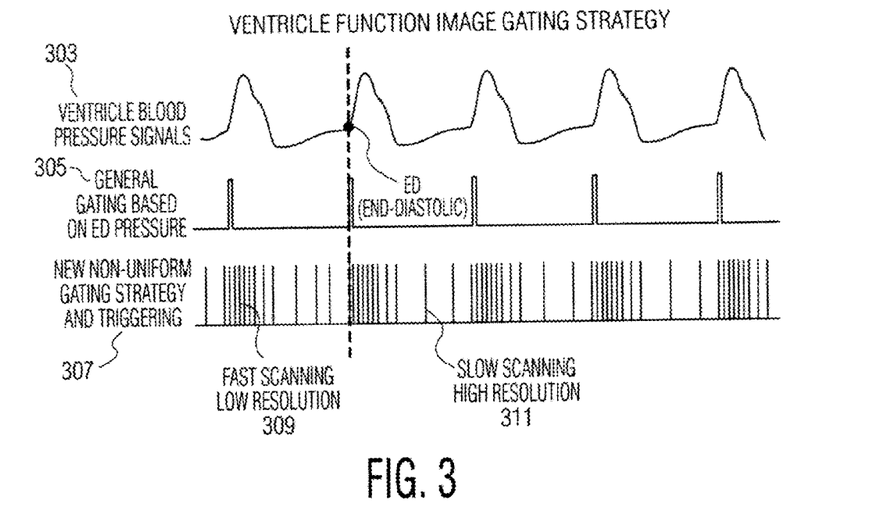
FIGS. 3 and 4 show non-uniform, non-periodic arrangements of pulses used for triggering image acquisition in an image acquisition system, according to invention principles.
Figure 4:
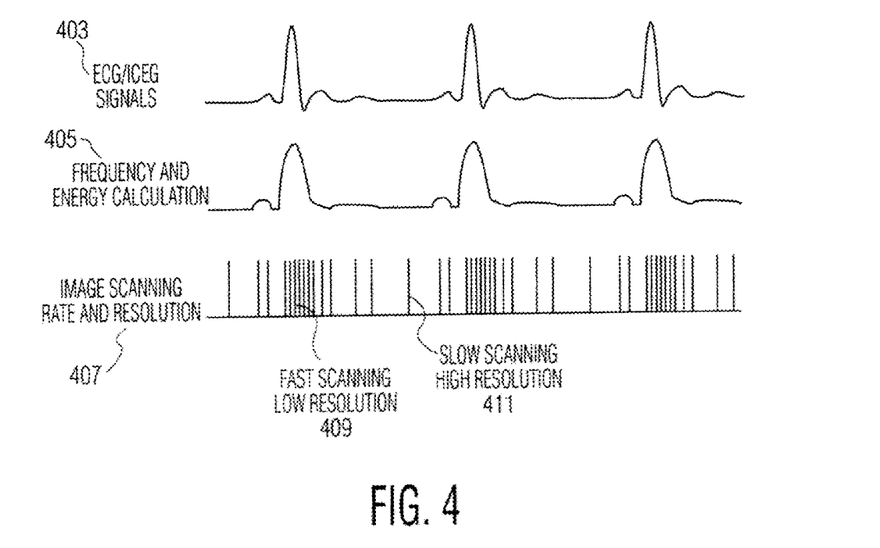

FIGS. 3 and 4 show non-uniform, non-periodic arrangements of pulses used for triggering image acquisition in image acquisition device 25. Invasive blood pressure (measured by a hemodynamic signal) is typical used for monitoring the internal blood pressure of cardiac chambers. FIG. 3 illustrates image acquisition involving invasive blood pressure of a left ventricle. Pressure waveform 303 shows systolic and diastolic pressure switching within a cardiac cycle and reflects the changes occurring within heart tissue activity. During a systolic stage, cardiac tissue is in a squeezing mode and there is substantial heart movement for which trigger generator 15 generates non-uniform, non-periodic sequence of pulses 307 using ED pressure gating signal 305. Pulse sequence 307 includes pulse sequence portion 309 used to trigger relatively fast image scanning and data acquisition, for example. During a diastolic stage, cardiac tissue is in a relatively relaxed mode with blood filling a heart chamber and there is less heart movement for which trigger generator 15 generates non-uniform, non-periodic pulse sequence portion 311 (using derived ED pressure gating signal 305) to trigger relatively slow image scanning and data acquisition, for example.

FIG. 4 illustrates image acquisition using an electrophysiological (ECG) signal to gate and synchronize acquisition. The time accuracy and position precision achieved using surface ECG signals is typically less than when using the invasive blood pressure signal of FIG. 3, but a surface ECG signal is easier to obtain and is non-invasive. ECG or ICEG waveform 403 shows electrical activity within a cardiac cycle and reflects the changes occurring within heart tissue activity. During a systolic stage when there is substantial heart movement, trigger generator 15 generates non-uniform, non-periodic sequence of pulses 407 including pulse sequence portion 409 from derived frequency and energy signal 405. Signal 405 is derived by trigger generator 15 from ECG and/or ICEG signal 403, for example. Pulse sequence portion 409 triggers relatively fast image scanning and data acquisition. During the diastolic stage when there is less heart movement, trigger generator 15 generates non-uniform, non-periodic pulse sequence portion 411 (using derived signal 405) to trigger relatively slow image scanning and data acquisition, for example.

Trigger generator 15 also uses vital sign signals in cardiac function based non-uniform image scanning and acquisition, such as a respiration signal for respiratory motion artifact rejection. This facilitates high quality and stable image acquisition. Trigger generator 15 also logically combines EP signals, Hemodynamic signals and vital sign signals for image acquisition triggering. For example, in order to provide a trigger for image acquisition that decreases the effect of patient movement and cardiac tissue squeezing effects, EP signals (ECG or ICEG) and respiration signals are used to generate a triggering pulse series for stable image scanning and acquisition. Trigger generator 15 obtains derivative and calculated signals for triggering using EP signals, Hemodynamic signals and vital sign signals and their combinations. These derivative signals include frequency, spectrum and energy signals and associated image acquisition triggering pulse sequences. The derived pulse sequences are generated in response to data indicating a type of clinical or diagnostic imaging procedure involved (e.g., coronary bypass) and processed to compensate for hardware delay and patient movement, for example.

Image data processor 36 also adaptively alters imaging parameters including image resolution, exposure time of a frame, image sensitivity and image system moving speed, for example. These parameters are dynamically adjusted within a heart cycle and over multiple heart cycles in response to data indicating a type of clinical or diagnostic imaging procedure involved. Processor 36 adaptively adjusts image resolution in response to data indicating a clinical application, diagnosis, treatment or diagnosis code and a type of radiological order, for example. An image of relatively low resolution may be mapped and aligned with a high resolution image to improve image quality and thereby high resolution MPEG (Motion Picture Expert Group) compatible real time image scanning is provided.

System 10 also employs cardiac function signal based non-uniform, non-periodic image scanning and acquisition for real time 3D image reconstruction. Heart tissue may be thought of as non-rigid matter which is moving unevenly in different directions. Hence tissue distortion from tissue movements may reduce resolution and precision of a 3D imaging volume reconstruction derived using 2D images. The system 10 functional signal based 3D image reconstruction advantageously avoids image reconstruction with non-synchronized image data of different heart cycle portions which distorts 3D reconstruction. A 3D image reconstruction dataset provided by system 10 facilitates diagnosis and characterization of cardiac function and tissue including volume/size of a chamber for a specific time (such as at a P wave, R wave, T wave) and maximum and minimum comparison of chambers and cardiac output.

Figure 5:
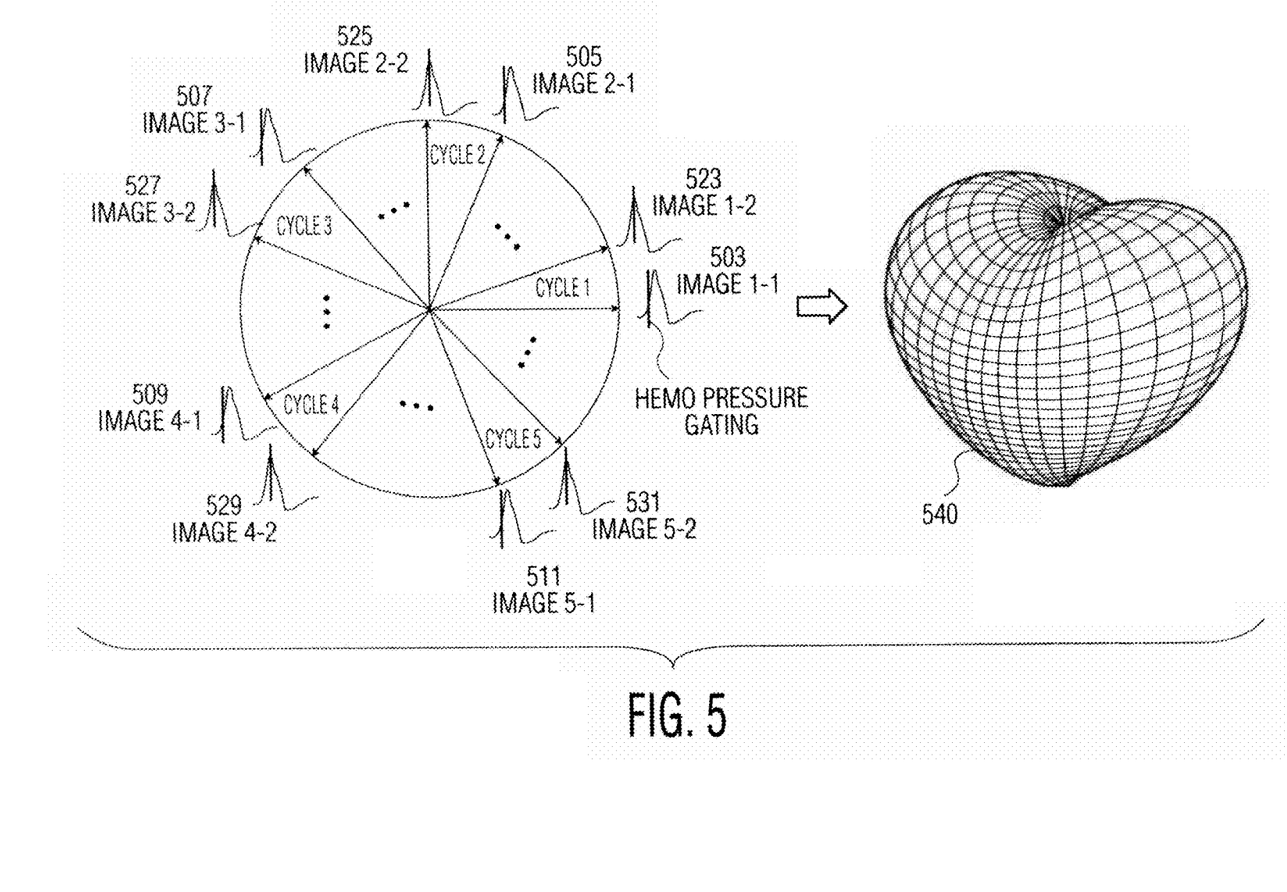
FIG. 5 illustrates non-uniform 3D heart image reconstruction based on non-uniform, non-periodic cardiac function signal gated image scanning and acquisition, according to invention principles.

FIG. 5 illustrates non-uniform 3D heart image reconstruction based on non-uniform, non-periodic cardiac function signal gated image scanning and acquisition. System 10 acquires images at the same time having the same time stamp in a heart cycle as indicated by an EP or hemodynamic signal. Image data processor 36 constructs a real time 3D image volume using 2D images acquired in different heart cycles but having the same time stamp point relative to start of a heart cycle. Image data processor 36 advantageously reconstructs 3D image volume 540 using synchronized images to improve 3D image quality. Imaging device 25 (FIG. 1) acquires 2D images at the same time position within individual heart beat cycles and under the same conditions of patient movement in response to a trigger signal provided by trigger generator 15. Thereby images are acquired from different angles of the heart to provide high precision 3D image reconstruction.

Trigger generator 15 employs precise heart cycle phase timing for individual image acquisition to ensure high pixel resolution and reliability of 3D image reconstruction. Processor 36 uses multiple sets of images acquired at multiple different points in a heart cycle to generate 3D image reconstruction 540 with a set of images being acquired at a particular point in a heart cycle determined by the trigger signal. Specifically, processor 36 generates 3D image reconstruction 540 using multiple 2D (two dimensional) image sets including a first and second set, for example. The first image set includes images acquired at substantially the same first point within five sequential (consecutive or non-consecutive) heart cycles (points 503, 505, 507, 509 and 511) gated by the trigger signal provided by generator 15 at a first particular phase of a heart cycle (having substantially the same first time stamp). The second image set includes multiple 2D images including images acquired at a second point within five sequential (consecutive or non-consecutive) heart cycles (points 523, 525, 527, 529 and 531) gated by the trigger signal provided by generator 15 at a second particular phase of a heart cycle (having substantially the same second time stamp). Processor 36 uses 2D images in reconstruction having substantially the same time stamp to minimize tissue distortion and motion effects to produce a 3D image volume dataset that facilitates detection of cardiac changes and abnormality.

Trigger generator 15 generates trigger signals to trigger image acquisition using an energy measure and also using frequency of an EP signal, for example. In one embodiment generator 15 derives an energy measure from an EP signal as follows.

$$\text{Energy\_based\_triggering\_frequency} = \frac{1}{\int_\tau \text{signal\_amplitude } dt},$$

τ is the smallest time duration for image scanning comprising multiple image acquisitions (which is determined by image hardware). Trigger generator 15 generates trigger signals to trigger image acquisition using frequency (e.g., dominant frequency) or signal amplitude of an EP signal. For example, such a signal may comprise a dominant frequency $$\text{Signal\_frequency\_based\_triggering\_frequency} = f(\text{signal\_frequency}),$$

where the dominant frequency is derived from an EP signal using measurement and calculation. For instance, if EP signal frequency is relatively high, generator 15 generates a trigger signal to initiate image acquisition at a relatively high image scanning speed to capture details of heart movement. If EP signal frequency is relatively low, generator 15 generates a trigger signal to initiate image acquisition at a relatively low image scanning speed to decrease redundant image scanning and radiation exposure. Trigger generator 15 may generate a trigger signal from a combination of different signals, for example, from a pressure parameter and ECG signal together to generate a trigger signal to optimize image accuracy and minimize motion effects from cardiac pacing.

Figure 6:
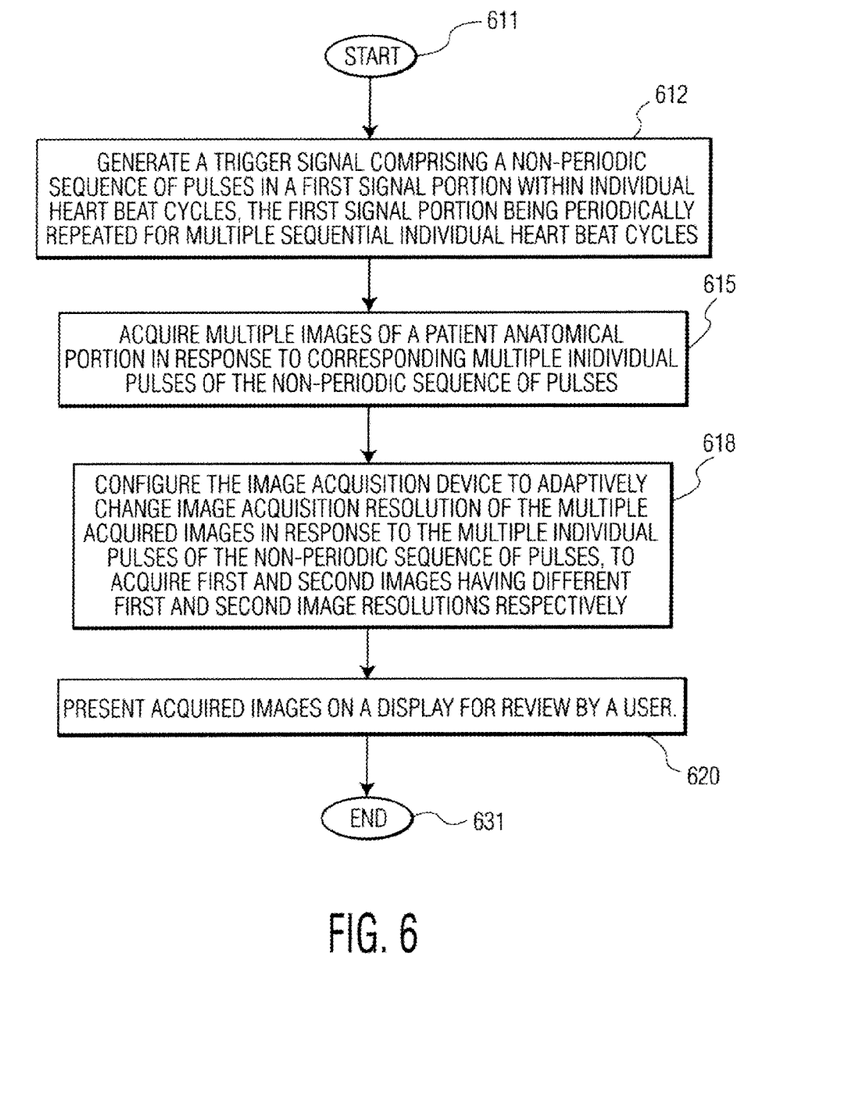
FIG. 6 shows a flowchart of a process used by an image acquisition system, according to invention principles.

FIG. 6 shows a flowchart of a process used by image acquisition system 10 (FIG. 1). In step 612 following the start at step 611, trigger generator 15 generates a trigger signal comprising a non-periodic (and non-uniform and non-linear) sequence of pulses in a first signal portion within individual heart beat cycles. The first signal portion is periodically or non-periodically repeated for multiple sequential (consecutive or non-consecutive) individual heart beat cycles. Trigger generator 15 generates the trigger signal by deriving the non-periodic sequence of pulses as a function of parameters including, (a) an ECG signal, (b) a vital sign signal, (c) a blood related signal, (d) a frequency signal, (e) a spectrum signal and (f) an energy signal. Image acquisition device 25 in step 615 acquires multiple images of a patient anatomical portion in response to corresponding multiple individual pulses of the non-periodic sequence of pulses.

In step 618, image acquisition controller 34 configures image acquisition device 25 to adaptively change image acquisition resolution of the multiple images acquired by image acquisition device 25 in response to (e.g., in synchronism with) the multiple individual pulses of the non-periodic sequence of pulses, to acquire first and second images having different first and second image resolutions respectively. The first and second images having different first and second image resolutions are acquired within the same or different heart cycles. In one embodiment, image acquisition controller 34 configures image acquisition device 25 to adaptively change radiation exposure time used in acquiring the multiple images acquired by image acquisition device 25 in response to (e.g., in synchronism with) the multiple individual pulses of the non-periodic sequence of pulses, to acquire first and second images having different exposure times respectively. In a further embodiment, image acquisition controller 34 configures image acquisition device 25 to adaptively change image sensitivity (e.g., luminance range, or contrast range) used in acquiring the multiple images acquired by image acquisition device 25 in response to (e.g., in synchronism with) the multiple individual pulses of the non-periodic sequence of pulses, to acquire first and second images having different sensitivity respectively. In another embodiment, image acquisition controller 34 configures image acquisition device 25 to adaptively change operational speed of movement of an X-ray emitter and detector used in acquiring the multiple images acquired by image acquisition device 25 in response to (e.g., in synchronism with) the multiple individual pulses of the non-periodic sequence of pulses, to acquire first and second images. Display processor 26 in step 620 presents acquired images on display 19 for review by a user. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system employs non-periodic, non-uniform and nonlinear patient monitoring signals in automatically adaptively varying image resolution, image scanning frequency, acquisition speed, exposure time, device operational movement speed, and imaging sensitivity of an imaging system such as an X-ray system. Further, the processes and applications may, in alternative embodiments, be located on one or more (e.g., distributed) processing devices on the network of FIG. 1. Any of the functions and steps provided in FIGS. 1-6 may be implemented in hardware, software or a combination of both.

What is claimed is:

1. A system for acquiring medical images of patient anatomy, comprising:
   means for generating a trigger signal comprising a non-periodic intra-heart cycle sequence of pulses non-periodically spaced in time within a first signal portion, said first signal portion occurring within individual heart beat cycles of a plurality of heart beat cycles and being periodically repeated for a plurality of sequential individual heart beat cycles;
   an image acquisition device configured for acquiring a plurality of images of a patient anatomical portion in response to a corresponding plurality of individual pulses of said non-periodic intra-heart cycle sequence of pulses; and
   a display processor configured for presenting acquired images on a display for review by a user.

2. A system according to claim 1, wherein
   said trigger signal comprises a non-periodic, non-uniform sequence of pulses.

3. A system according to claim 2, wherein
   said trigger signal comprises a non-periodic, non-uniform, non-linear sequence of pulses non-periodically spaced in time within said first signal portion.

4. A system according to claim 1, wherein
   said trigger signal is generated by deriving said non-periodic intra-heart cycle sequence of pulses as a function of parameters including at least two of, (a) an ECG signal, (b) a vital sign signal and (c) a blood related signal.

5. A system according to claim 4, wherein
   said trigger signal is generated by deriving said non-periodic intra-heart cycle sequence of pulses as a function of parameters including at least one of, (a) a frequency signal, (b) a spectrum signal and (c) an energy signal.

6. A system according to claim 1, wherein
   said image acquisition device adapts image resolution comprising number of pixels of individual images of said plurality of images in synchronism with said plurality of individual pulses of said non-periodic intra-heart cycle sequence of pulses.

7. A system according to claim 1, wherein
   said image acquisition device adapts exposure time of at least one image of said plurality of images in synchronism with said plurality of individual pulses of said non-periodic intra-heart cycle sequence of pulses.

8. A system according to claim 1, wherein
   said image acquisition device adapts image sensitivity of at least one image of said plurality of images in synchronism with said plurality of individual pulses of said non-periodic intra-heart cycle sequence of pulses.

9. A system according to claim 1, wherein
   said image acquisition device adapts imaging device operational speed for at least one image of said plurality of images in synchronism with said plurality of individual pulses of said non-periodic intra-heart cycle sequence of pulses.

10. A system for acquiring medical images of patient anatomy, comprising:
    means for generating a trigger signal comprising a non-periodic intra-heart cycle sequence of pulses non-periodically spaced in time within a first signal portion within individual heart beat cycles of a plurality of heart beat cycles, said first signal portion being non-periodically repeated for a plurality of sequential individual heart beat cycles;

an image acquisition device configured for acquiring a plurality of images of a patient anatomical portion in response to a corresponding plurality of individual pulses of said non-periodic intra-heart cycle sequence of pulses; and a display processor configured for presenting acquired images on a display for review by a user.

11. A system for acquiring medical images of patient anatomy, comprising:

a trigger generator configured for generating a trigger signal comprising a non-periodic sequence of pulses non-periodically spaced in time within a first signal portion within individual heart beat cycles, said first signal portion being periodically repeated for a plurality of sequential individual heart beat cycles;

an image acquisition device configured for acquiring a plurality of images of a patient anatomical portion in response to a corresponding plurality of individual pulses of said non-periodic sequence of pulses;

an image acquisition controller for configuring said image acquisition device to adaptively change image acquisition resolution comprising number of pixels of individual images of said plurality of images acquired by said image acquisition device in response to said plurality of individual pulses of said non-periodic sequence of pulses, to acquire first and second images having different first and second image resolutions respectively; and a display processor configured for presenting acquired images on a display for review by a user.

12. A system according to claim 11, wherein said first and second images having different first and second image resolutions are acquired within the same heart cycle.

13. A system according to claim 11, wherein said image acquisition controller configures said image acquisition device to adaptively change radiation exposure time used in acquiring said plurality of images acquired by said image acquisition device in response to said plurality of individual pulses of said non-periodic sequence of pulses, to acquire first and second images having different exposure times respectively.

14. A system according to claim 11, wherein said image acquisition controller configures said image acquisition device to adaptively change image sensitivity used in acquiring said plurality of images acquired by said image acquisition device in response to said plurality of individual pulses of said non-periodic sequence of pulses, to acquire first and second images having different sensitivity respectively.

15. A system according to claim 11, wherein said image acquisition controller configures said image acquisition device to adaptively change operational speed of movement of an X-ray emitter and detector used in acquiring said plurality of images acquired by said image acquisition device in response to said plurality of individual pulses of said non-periodic sequence of pulses, to acquire first and second images.

16. A system according to claim 11, wherein said trigger signal comprises a non-periodic, non-uniform sequence of pulses.

17. A method for acquiring medical images of patient anatomy, comprising the steps of:

generating a trigger signal comprising a non-periodic intra-heart cycle sequence of pulses non-periodically spaced in time within a first signal portion within individual heart beat cycles of a plurality of heart beat cycles, said first signal portion being periodically repeated for a plurality of sequential individual heart beat cycles;

acquiring a plurality of images of a patient anatomical portion in response to a corresponding plurality of individual pulses of said non-periodic intra-heart cycle sequence of pulses; and presenting acquired images on a display for review by a user.

* * * * *